United States Patent
Nakajima

(10) Patent No.: US 10,137,097 B2
(45) Date of Patent: Nov. 27, 2018

(54) NON-PEPTIDIC GAPDH AGGREGATION INHIBITOR

(71) Applicant: Osaka Prefecture University Public Corporation, Sakai-shi, Osaka (JP)

(72) Inventor: Hidemitsu Nakajima, Sakai (JP)

(73) Assignee: OSAKA PREFECTURE UNIVERSITY PUBLIC CORPORATION, Osaka (JP)

( * ) Notice: Subject to any disclaimer, the term of this patent is extended or adjusted under 35 U.S.C. 154(b) by 0 days.

(21) Appl. No.: 15/574,651

(22) PCT Filed: Jun. 8, 2016

(86) PCT No.: PCT/JP2016/066999
§ 371 (c)(1),
(2) Date: Nov. 16, 2017

(87) PCT Pub. No.: WO2016/199796
PCT Pub. Date: Dec. 15, 2016

(65) Prior Publication Data
US 2018/0116981 A1   May 3, 2018

(30) Foreign Application Priority Data

Jun. 8, 2015 (JP) ................. 2015-116140

(51) Int. Cl.
| | |
|---|---|
| *A61K 31/16* | (2006.01) |
| *A61K 31/10* | (2006.01) |
| *A61P 25/28* | (2006.01) |
| *A61P 25/16* | (2006.01) |
| *A61K 31/164* | (2006.01) |
| *C07C 323/57* | (2006.01) |

(52) U.S. Cl.
CPC ............. *A61K 31/16* (2013.01); *A61K 31/10* (2013.01); *A61K 31/164* (2013.01); *A61P 25/16* (2018.01); *A61P 25/28* (2018.01); *C07C 323/57* (2013.01)

(58) Field of Classification Search
CPC ......... A61K 31/16; A61K 31/10; A61P 25/28; A61P 25/16
USPC ....................................................... 514/676
See application file for complete search history.

(56) References Cited

FOREIGN PATENT DOCUMENTS

| JP | 2001-525800 A | 12/2001 | |
|---|---|---|---|
| JP | 2002-226457 A | 8/2002 | |
| JP | 2002-529404 A | 9/2002 | |
| JP | 2009-286755 A | 12/2009 | |
| JP | 2013-241402 A | 12/2013 | |
| WO | WO-0027378 A2 * | 5/2000 | ........... A61K 31/165 |

OTHER PUBLICATIONS

International Search Report dated Jul. 12, 2016, issued in counterpart International Application No. PCT/JP2016/066999 (2 pages).

* cited by examiner

*Primary Examiner* — Kristin A Vajda
(74) *Attorney, Agent, or Firm* — Westerman, Hattori, Daniels & Adrian, LLP

(57) ABSTRACT

[Problem] Provided is a non-peptide compound which can be used as a GAPDH aggregation inhibitor. [Solution] Provided is a GAPDH aggregation inhibitor including as an active ingredient a compound represented by the chemical formula 1 wherein $R_1$, $R_2$, and $R_3$ are each independently a hydrogen atom, a halogen atom, or an aliphatic hydrocarbon group having a carbon number of from 1 to 10, a polysulfurized derivative thereof, or a pharmaceutically acceptable salt thereof. The present compound has a GAPDH aggregation inhibitory activity to suppress intracerebral aggregation of various proteins involved in cerebral neurodegenerative diseases, thereby contributing to improvement in various brain neurological diseases associated with aggregation of these proteins such as Alzheimer's disease, Parkinson's disease, and cerebral infarction, and prevention of advanced seriousness of these diseases.

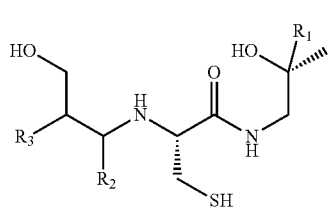

[Formula 1]

3 Claims, 7 Drawing Sheets
Specification includes a Sequence Listing.

[Fig. 2]
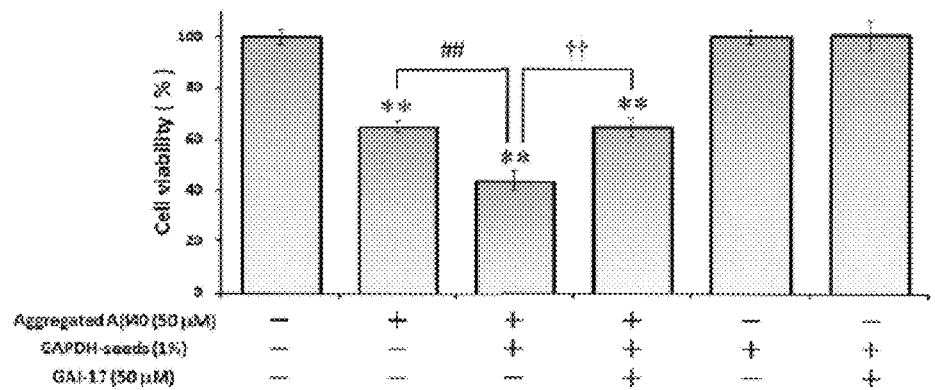
[Fig. 3]
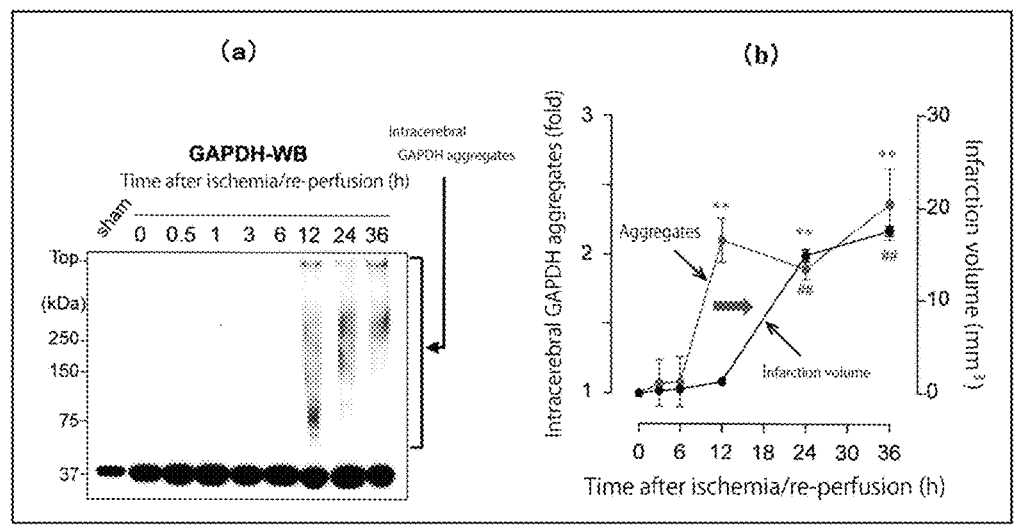

[Fig. 4]
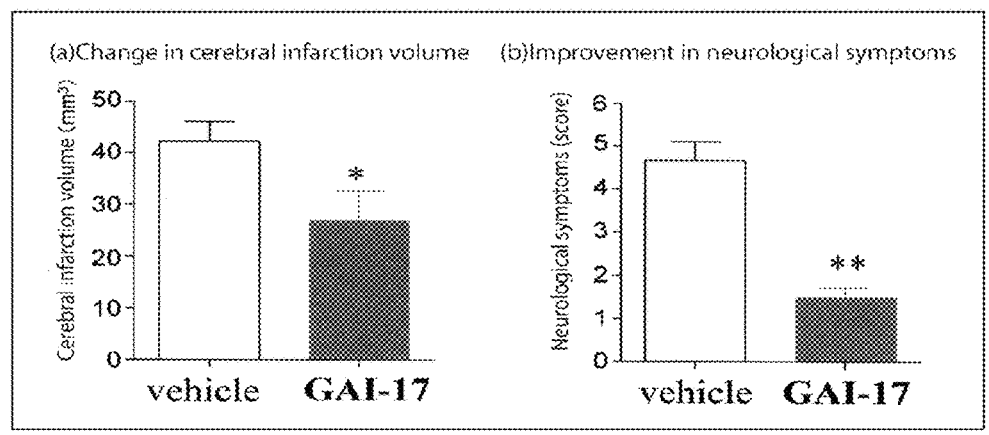
[Fig. 5]
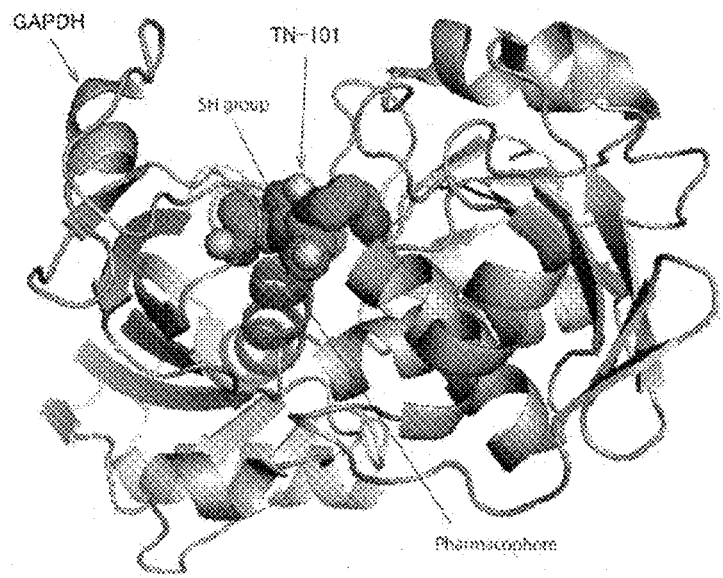

[Fig. 6]
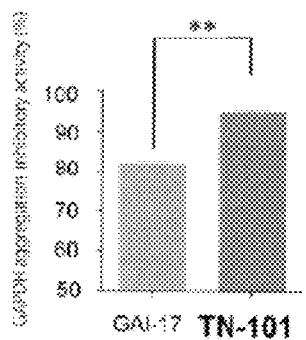
[Fig. 7]
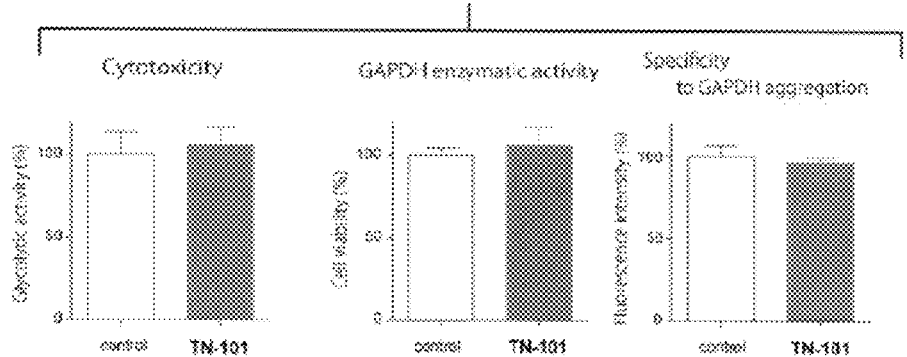

[Fig. 8]
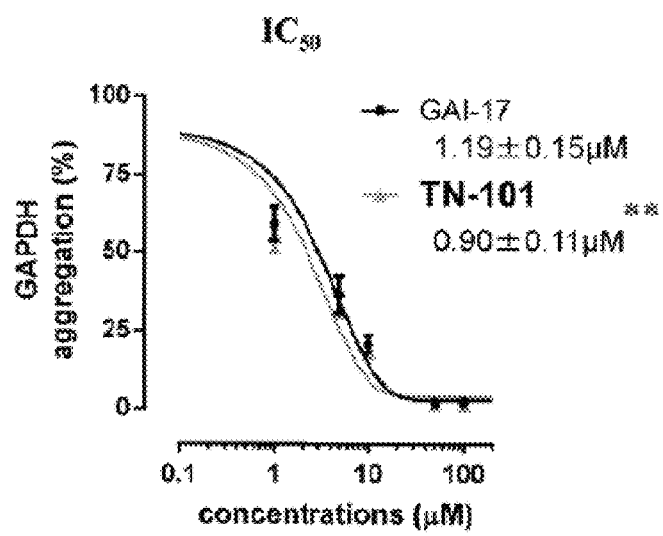

NON-PEPTIDIC GAPDH AGGREGATION INHIBITOR

TECHNICAL FILED

The present invention relates to a non-peptide aggregation inhibitor of GAPDH (glyceraldehyde-3-phosphate dehydrogenase).

BACKGROUND ART

Alzheimer's disease, which causes cognitive disorder as a major symptom, requires immediate attention to take countermeasures. The correction between amyloidosis such as Alzheimer's disease and aggregation of GAPDH suggests that inhibition of GAPDH aggregation may prevent aggregation or deposition of amyloid β. In view of such circumstances, the present inventors have found that a peptide consisting of 10 to 20 amino acid residues with a specific amino acid sequence can inhibit aggregation of GAPDH. This finding has been filed as a patent application (Patent Document 1).

However, peptides are decomposed in the gastrointestinal tract, and rapidly metabolized in the body. Further, peptides are generally accepted to have poor cerebral internalization even via intravenous administration. Moreover, peptides suffer from difficult synthesis and purification. For these reasons, a peptide-like but non-peptide compound (a peptide mimic) is desired.

CITATION LIST

Patent Document

Japanese Unexamined Patent Application Publication No. 2013-241402

SUMMARY OF INVENTION

Technical Problem

The present invention is made in view of the circumstances described in background art. After conducting extensive studies based on the peptide disclosed in Patent Document 1, the present inventors now find that a peptide consisting of even fewer amino acid residues can suppress aggregation of GAPDH. Further the present inventors now find a compound capable of selectively inhibiting aggregation of GAPDH after conducting modeling of various compounds starting from the above peptide. That is, an object of the present invention is to provide a novel non-peptide compound which can be used as a GAPDH aggregation inhibitor.

Solution to Problem

A compound according to the present invention is represented by the following chemical formula 1 (Formula 1) or a polysulfurized derivative thereof, and may be used as a GAPDH aggregation inhibitor. In the formula, $R_1$, $R_2$, and $R_3$ are each independently a hydrogen atom, a halogen atom, or an aliphatic hydrocarbon group having a carbon number of from 1 to 10. Further, the compound according to the present invention may be a pharmaceutically acceptable salt thereof.

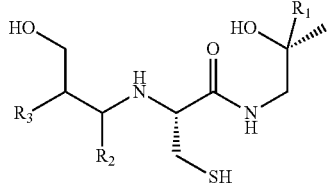

[Formula 1]

Advantageous Effects of Invention

The present invention can provide a novel GAPDH aggregation inhibitor as a non-peptide compound.

BRIEF DESCRIPTION OF DRAWINGS

FIG. 2 shows protective effects of a GAI-17 peptide on amyloid β40 induced PC12 cell death. In the figure, "**" means that there was a significant difference (1% significance level) against a control, and "##" and "††" mean that there was a significant difference (1% significance level) between subject groups.

FIG. 3 shows the relationship between GAPDH aggregation and cerebral infarction in a stroke model. (a) shows an image from Western blotting indicating formation of intracerebral GAPDH aggregates, and (b) shows the relationship between formation of intracerebral GAPDH aggregates and cerebral infarction volume.

FIG. 4 shows cerebroprotective effects of the GAI-17 peptide. (a) shows the change in cerebral infarction volume, and (b) shows the improvement in neurological symptoms.

FIG. 5 shows a pharmacophore model with the compound TN-101 bound to GAPDH.

FIG. 6 shows results from a first screening for the compound TN-101.

FIG. 7 shows results from a second screening for the compound TN-101.

FIG. 8 is a graph illustrating results from measuring a GAPDH aggregation inhibitory activity ($IC_{50}$) of the compound TN-101. In the figure, "**" means that there was a significant difference (1% significance level) against the GAI-17 peptide.

DESCRIPTION OF EMBODIMENTS

The compound according to the present invention is a compound represented by the following chemical formula 1 (Formula 1) or a polysulfurized derivative thereof. In the formula, $R_1$, $R_2$, and $R_3$ are each independently a hydrogen atom, a halogen atom, or an aliphatic hydrocarbon group having a carbon number of from 1 to 10. The halogen atom may be a fluorine atom, a chlorine atom, a bromine atom, or an iodine atom. The aliphatic hydrocarbon group may be a saturated or unsaturated hydrocarbon group, or may be a linear or branched hydrocarbon group. The aliphatic hydrocarbon group may be, for example, a methyl group, an ethyl group, an n-propyl group, an isopropyl group, an n-butyl group, an isobutyl group, a sec-butyl group, or a tert-butyl group. In the present invention, the polysulfurized derivative refers to a compound as represented by the chemical formula 2 (Formula 2 wherein n is an integer of 1 or more) or the chemical formula 5 (Formula 5 wherein n is an integer of 1 or more) where one or more sulfur atoms (polysulfur) are further added to the sulfur atom on the compound represented by the chemical formula 1 and a derivative as represented by the chemical formula 3 (Formula 3 wherein n is an integer of 1 or more) or the chemical formula 6 (Formula 6 wherein n is an integer of 1 or more) where two molecules of the compound represented by the chemical formula 1 are attached together through one or more sulfur atoms (polysulfur). Further, the compound according to the present invention may be in a form of a pharmaceutically acceptable salt. The above salt may be, for example, a hydrochloride, a sulfate, a maleate, an oleate, or a fumarate. It is noted that a compound represented by the chemical formula 5 or 6 corresponds to a compound in which $R_1$, $R_2$, and $R_3$ are each a hydrogen atom in the chemical formula 2 or 3, respectively.

[Formula 1]

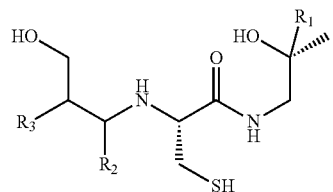

[Formula 2]

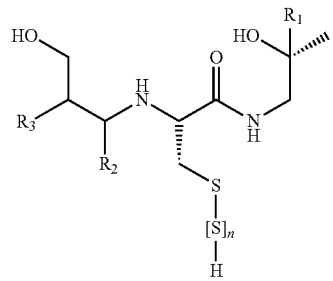

[Formula 5]

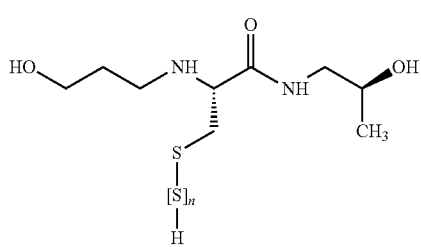

[Formula 3]

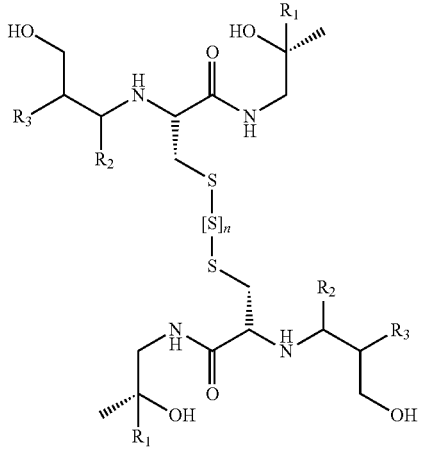

[Formula 6]

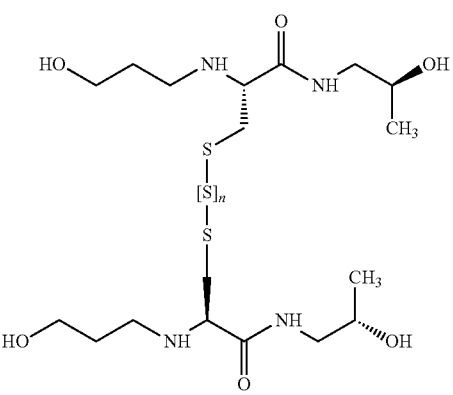

Figure 1A:
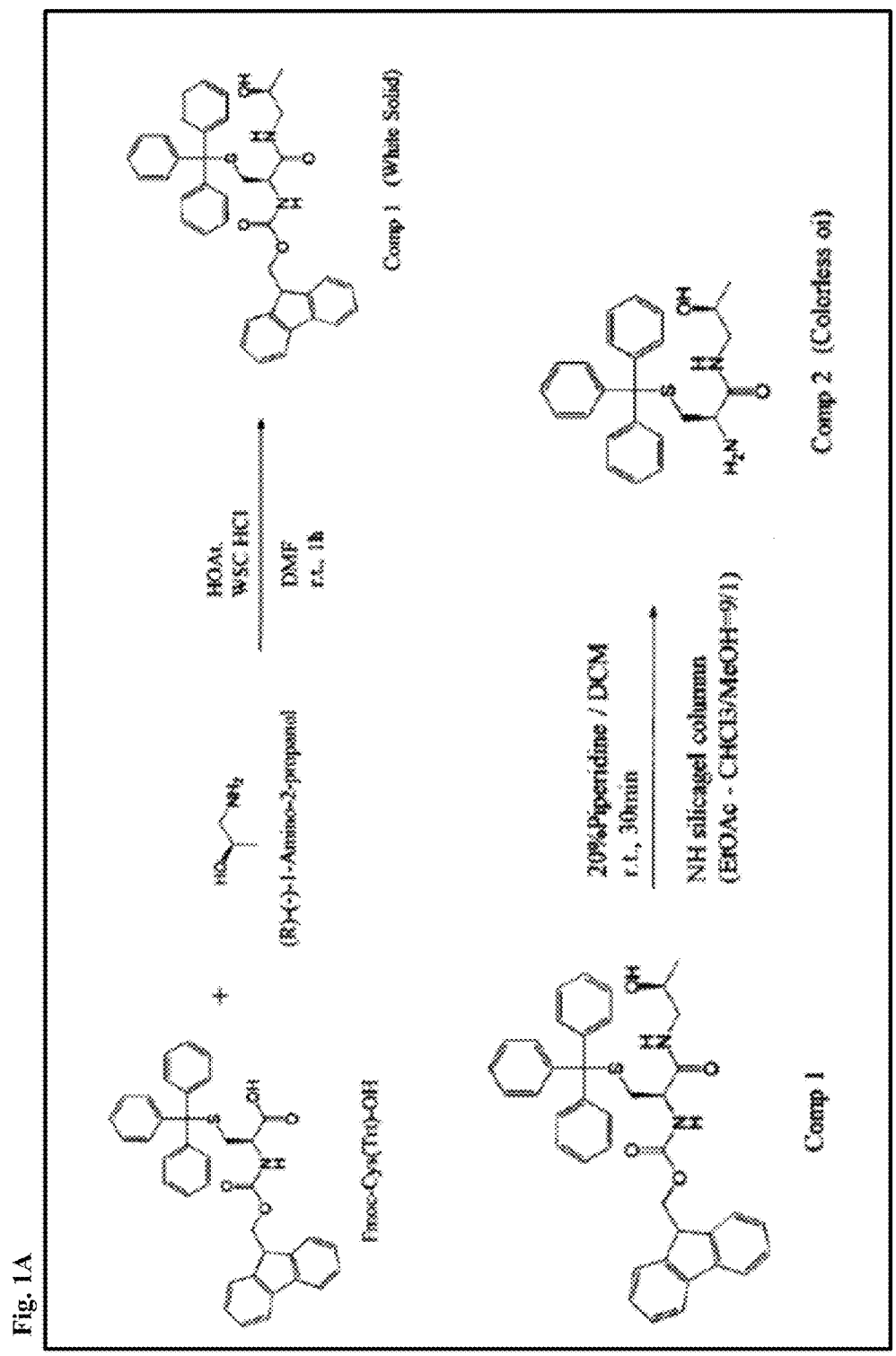
FIGS. 1A to 1C show a synthesis pathway of a compound TN-101.
Figure 1B:
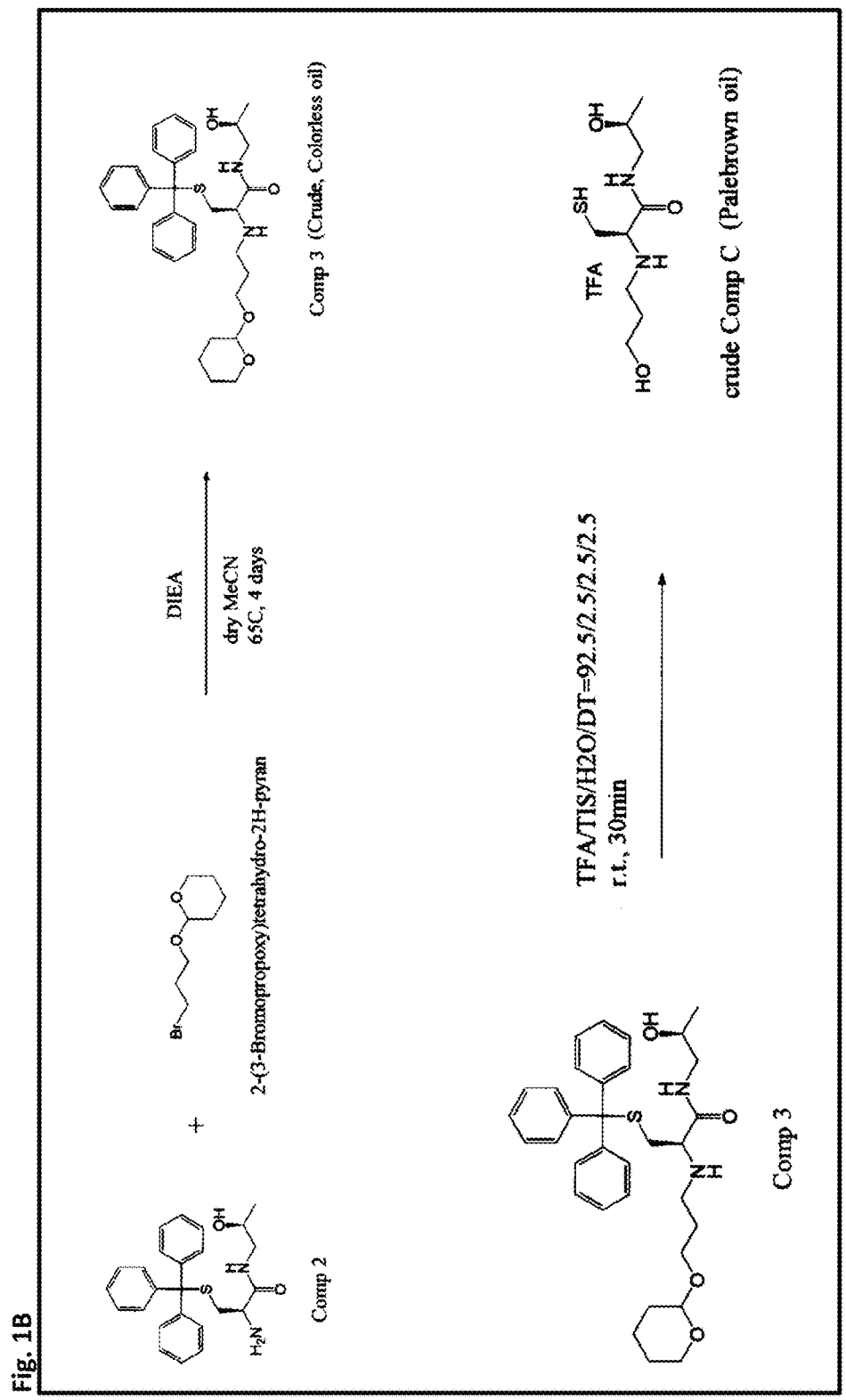
Figure 1C:
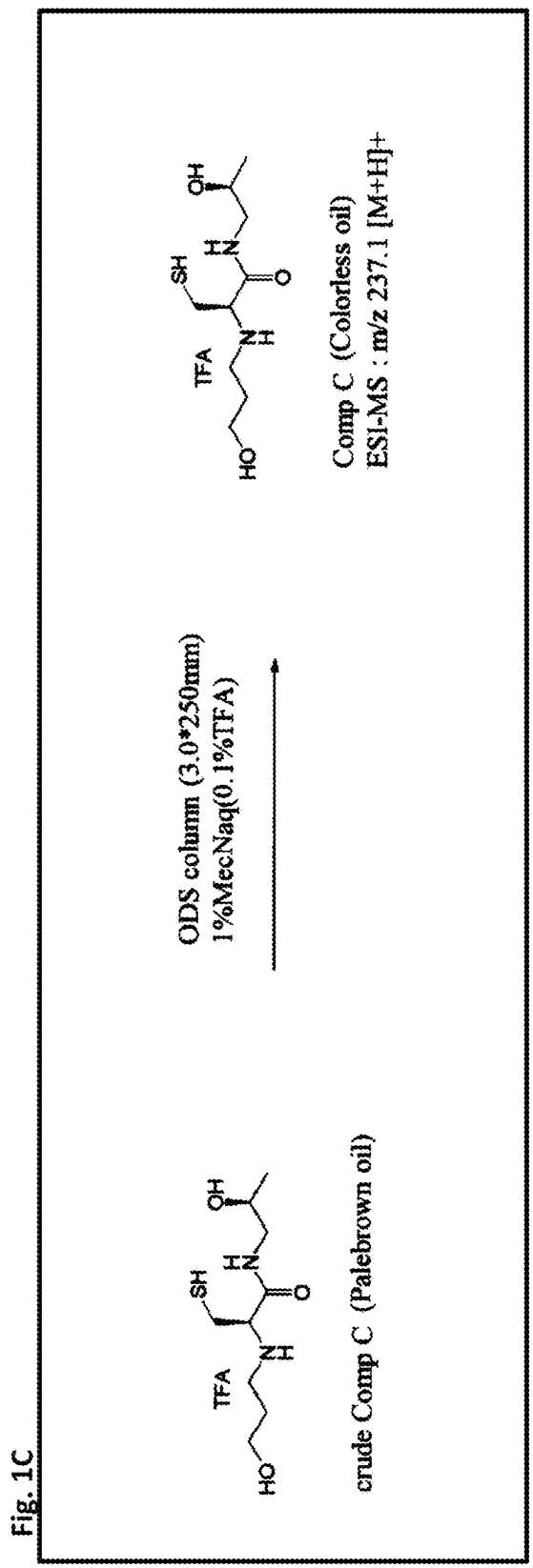

The compound represented by the chemical formula 1 may easily be synthesized by a common synthesis method. For example, a synthesis method as shown in FIGS. 1A to 1C may be used. It is noted that reaction conditions, reagents, and solvents shown in FIGS. 1A to 1C are merely illustrative, and a person skilled in the art would otherwise appropriately select preferred conditions, reagents, and solvents. The aforementioned polysulfurized derivative may be produced by a known method, for example, a method described in an article by Ida et al. (Ida T, Sawa et al., Reactive cysteine persulfides and S-polythiolation regulate oxidative stress and redox signaling, *Proc. Natl. Acad. Sci. USA.*, 2014, 111(21), 7606-7611).

The compound according to the present invention has a GAPDH aggregation inhibitory activity, and may be used for prevention, treatment, or improvement of various cerebral neurodegenerative diseases or conditions thereof. The cerebral neurodegenerative diseases may include, for example, Alzheimer's disease, Huntington disease, Parkinson's disease, and cerebral infarction. The SH group of the present compound enters into a biding pocket formed around Cys-152 at the active center of GAPDH to form an S—S bond with Cys-152 of GAPDH. This enables the present compound to inhibit oligomerization (aggregation) of GAPDH. Therefore, substituents $R_1$, $R_2$, and $R_3$ may be selected with reference to a pharmacophore model, and have more than 10 carbon atoms when the present compound is intended for use as a pharmaceutical product. Aggregation of GAPDH can prevent aggregation and deposition of various proteins involved in cerebral neurodegenerative diseases, for example, amyloid β in the case of Alzheimer's disease. Further, GAPDH aggregates may be formed before cerebral infarction when cerebral blood flow obstruction occurs. Therefore, development or progression of cerebral infarction can be prevented.

The present compound may typically foe prepared in a form of a pharmaceutical composition when used as a pharmaceutical product. The pharmaceutical composition may be administered via various methods such as transdermal, intravenous, intramuscular, and transrectal administrations in addition to direct intraventricular administration. The pharmaceutical composition can be formulated into a dosage form preferred for a corresponding route of administration. There is no particular limitation for the dosage form, but it may be, for example, a powder, a granule, a tablet, a capsule, an oral liquid, an injectable, a spray, an ointment, or a plaster.

The pharmaceutical composition according to the present invention may contain the compound according to the present invention, a carrier required for formulation, and an auxiliary agent other than the carrier. The carrier required for formulation may be, for example, an excipient such as starch, lactose, and sucrose; purified water for liquid preparations; injectable purified water for injectable preparations; an ointment base such as Vaseline and lanolin used for external preparations; or the like. The auxiliary agent other than the carrier may be, for example, a binder such as tragacanth gum and gelatin; a lubricant such as magnesium stearate and talc; a disintegrant such as low-substituted hydroxypropylcellulose; a coating agent such as methyl cellulose and hydroxypropylcellulose; a pH adjuster; a stabilizer; an emulsifying agent; or the like.

The dosage amount of a compound may be appropriately determined depending on the compound to be administered, the disease and conditions of a patient, the route of administration, the age and weight of the patient, and the like. The loading amount in a pharmaceutical composition may be appropriately adjusted depending on a dosage form so as to satisfy a required dosage level. The loading amount is generally about 0.0001% to 50%, but not limited to this range.

Hereinafter, the present invention will be described specifically with reference to Examples, but the present invention shall not be limited to Examples below.

acid sequence of SCT was selected. Then, an $IC_{50}$ value for the GAPDH aggregation inhibitory activity was determined for the selected peptide GAI-17. Results therefrom, are shown in Table 1.

(First Screening)

As the first screening, GAPDH aggregation inhibitory activities, which represents potency, were measured. According to a method described in Patent Document 1, a peptide was added to a solution in which 5 μM purified human GAPDH was dissolved in Buffer G2 so that, the concentration of the peptide was 50 μM, and then incubated at 37° C. for 48 hours. Then the aggregation inhibitory rate of GAPDH was measured using the turbidity (absorbance at 405 nm) of the solution.

(Second Screening)

As the second screening, A) the viability of PC12 cells in the presence of a peptide, which represented cytotoxicity, B) effects on the GAPDH enzymatic activity, which represented side effects, and C) effects on amyloid formation, which represented specificity, were each investigated.

A) Cytotoxicity

PC12 cells cultured to 80% confluence were cultured at 37° C. for 72 hours in the presence of 50 μM peptide, and the cell viability was measured in accordance with the conventional method.

B) Side Effects

A 10 μM peptide was added to 0.01 μM purified human GAPDH, and the enzymatic activity of GAPDH was measured in accordance with a method described in Patent Document 1.

C) Specificity

A solution containing 25 μM amyloid β23-35 was incubated at 37° C. for 1 hour, and formation of amyloid aggregates was evaluated using the fluorescence intensity from the solution in accordance with a method described in Patent Document 1.

(Third Screening)

As the third screening, cytoprotective effects were investigated, which represented effectiveness. Cytoprotective effects on Aβ1-40 induced PC12 cell death were investigated in accordance with a method described in Patent Document 1.

TABLE 1

| | | 1st. Screening Potency Inhibitory activity (%) (50 μM at 48 h) in vitro | 2nd. Screening | | | 3rd. Screening Effectiveness Cytoprotection (%) in Aβ40-treated PC12 cells | $IC_{50}$ (μM) (MEAN ± S.E.) in vitro |
|---|---|---|---|---|---|---|---|
| | | | Cyrotoxicity Cell viability (%) in PC12 cells | Side effect Effect on GAPDH Activity (%) in vitro | Specificity Effect on Aβ25-35 amyloidogenesis (%) in vitro | | |
| GAI | Sequence | | | | | | |
| 1 | SNASCTTNAL | 53.2 ± 1.73 | 104 ± 1.37 | 105 ± 1.80 | 103 ± 9.94 | 48.0 ± 3.85 | 50.0 ± 0.20 |
| 17 | SCT | 97.7 ± 1.48 | 100 ± 0.76 | 97.9 ± 0.72 | 102 ± 6.39 | 99.4 ± 1.21 | 1.19 ± 0.15 |

Example 1

[Downsizing of Peptide]

A peptide as a lead compound was searched before producing a peptide mimic. Various peptides were synthesized in which several amino acids at the N and C termini were deleted from GAI-1 (SEQ ID NO: 1) having an amino acid sequence as shown in Table 1. Each of the synthesized peptides was subject to a first, second, and third screenings as described below, and a peptide (GAI-17) having an amino Next, the protective effects of GAI-17 on amyloid β induced cell death in the presence of GAPDH-Seeds (amyloid-like fiber of GAPDH) which may promote amyloid formation, and the cerebroprotective effects of GAI-17 were investigated according to the method described below.

(Protective Effects on Amyloid β Induced Cell Death in the Presence of GAPDH-Seeds)

Cytoprotective effects on Aβ1-40 induced PC12 cell death were investigated in the presence of GAPDH-Seeds (1%)

and GAI-17 (50 µM) according to a method described in Patent Document 1. Results therefrom are shown in FIG. 2.

(Cerebroprotective Effects)

For cerebroprotective effects, the changes in cerebral infarction volume and the improvement in neurological symptoms were studied in a stroke model (MCAO). To a stroke model mouse, 60 nmol/mouse of a peptide was intraventricularly administered, and the reduction in cerebral infarction volume and the improvement in neurological symptoms after 24 hours were determined. The stroke model mouse was prepared in accordance with a method by of Andrabi et al. (Andrabi et al., *Nat Med.*, 2011, June; 17(6): 692-9). A mouse was maintained under the state of ischemia for 30 minutes, and then perfusion was re-started. The cerebral infarction volume was measured 36 hours after ischemia started. Further, in accordance with the method by Andrabi et al. (supra), a neurological score was determined for neurological symptoms of the mouse to evaluate the improvement in neurological symptoms.

Aggregation of GAPDH is generally accepted to be involved in not only aggregation of β amyloid but also aggregation of proteins involved in other cerebral neurodegenerative diseases (for example, α-synuclein in Parkinson's disease and huntingtin in Huntington's disease) (Tsuchiya K. et al., *Eur J Neurosci.*, 21, 317-26; Bae B I. et al., *Proc Natl Acad Sci USA.*, 103, 3405-9; and others). When the relationship with aggregation of GAPDH in the context of cerebral infarction as one of the cerebral neurodegenerative diseases was studied, formation of GAPDH aggregates was observed in the brain from about 12 hours after ischemia/re-started perfusion, and an increase in cerebral infarction volume was observed following the formation of GAPDH aggregates as shown in FIG. 3. In contrast, administration of the peptide was found to decrease cerebral infarction volume and improve neurological symptoms after 24 hours (FIG. 4). These results suggest that inhibition of GAPDH aggregation may prevent deterioration of neurological symptoms which have been caused by blood flow obstruction such as stroke, or may improve neurological symptoms which have been caused by blood flow obstruction such as stroke. In particular, administration within 6 hour after stroke is likely to lead to prevention of advanced seriousness.

Example 2

(Synthesis of Compound TN-101)

Next, the peptide GAI-17 was used as a lead compound to design a compound (TN-101) in which $R_1$, $R_2$, and $R_3$ in the chemical formula 1 were each a hydrogen atom, and the compound TN-101 was synthesized according to a scheme shown in FIGS. 1A to 1C.

At room temperature, 3 g of 9-fluorenyl carbomethoxy-S-trityl-L-cysteine (Fmoc-Cys(Trt)-OH) and 0.58 g of (R)-(-)-1-amino-2-propanol were allowed to react in 35 ml of dimethylformamide containing 0.8 g of acetic acid and 1.28 g of water-soluble carbodiimide·HCl for 1 hour to obtain 3.5 g of a compound 1. Next, 1 g of the compound 1 was dissolved in 35 ml of dichloromethane containing 20% piperidine, and allowed to react at room temperature for 30 minutes. Subsequently, the reaction product was allowed to adsorb on a NH silica gel column, and then eluted with an eluent (a mixture of equal volume of ethyl acetate and chloroform:methanol=9:1) to obtain 0.69 g of a compound 2. The compound 2 in an amount of 0.69 g and 2-(3-bromopropoxy)tetrahydro-2H-pyran in an amount of 4.29 g were allowed to react in 40 ml of dry acetonitrile containing 2.34 mL of 1-ethyl-3-(3-dimethylaminopropyl) carbodiimide·HCl to obtain 1.94 g of a compound 3. The compound 3 in an amount of 1.94 g was allowed to react in 10 ml of a mixture of trifluoroacetic acid/triisopropyl silane/water/dodecanethiol at room temperature for 30 minutes to obtain 0.41 g of a crude compound C (crude TN-101). The crude compound C in an amount of 82 mg was allowed to adsorb on an ODS column, and then eluted with an eluent (1% aqueous acetonitrile containing 0.1% trifluoroacetic acid) to obtain 34 mg of a trifluoroacetate of the purified compound C (TN-101). Electrospray ionization mass spectrometry and NMR revealed that this compound had a molecular weight of 237.1 (salt free).

As shown in FIG. 5, simulations showed that the compound TN-101 entered into a hydrophobic binding pocket formed around Cys-152 as the aggregation active center of GAPDH, and the thiol group of Cys-152 on GAPDH was protected when accessed by the SH group of TN-101, resulting in blocked oligomerization of GAPDH.

(Effectiveness of TN-101)

The compound TN-101 was subjected to the first and second screenings in a similar way as in Example 1. Results indicated that TN-101 showed an aggregation inhibitory activity superior to that of the lead compound (the GAI-17 peptide) in the first screening (FIG. 6), and also showed cytotoxicity and an uninhibited GAPDH enzymatic activity comparable with or smaller than those of the lead compound in the second screening (FIG. 7). Further, the $IC_{50}$ value (0.90±0.11 µM) for the GAPDH aggregation inhibitory activity was also significantly smaller than that of the lead compound (FIG. 8), suggesting that TN-101 was a suitable GAPDH aggregation inhibitor.

Example 3

(Synthesis of Polysulfurized Derivative)

A thiol substance having an in vivo antioxidative activity such as glutathione (GSH) may form an S—S bond (disulfide bond) to become a dimer (GS-SG) under oxidative stress environments such as stroke. Therefore, the antioxidative activity may be lost, resulting in decreased in vivo stability. Meanwhile, a thiol substance may readily be polysulfurized with hydrogen sulfide produced in vivo, and a polysulfurized derivative appears to have an increased antioxidative activity and in vivo stability as compared with a monomer and a dimer (the article by Ida et al.). The article states that among polysulfurized derivatives (GS-(S)n-SG: n≥1) of glutathione, for example, GS-SS-GS shows the height in vivo stability and antioxidative activity. Accordingly, for TN-101 as a thiol compound (referred to as "TNSH"), a polysulfurized derivative (TNS-(S)n-STN: n is an integer of 1 or more) was synthesized for the purpose of increasing the in vivo stability and activity.

A polysulfurized derivative of the compound 1 was synthesized in accordance with a method described in the article by Ida et al. Aqueous TH-101 (20 mM) and 20 mM sodium hydrogensulfide (NaHS) were mixed in the presence of a 20 mM iodo ($I_2$) solution dissolved in a 20 µM Tris-HCl buffer solution (pH 7.4), and allowed to react at room temperature for 15 minutes. The reaction liquid was developed by reverse phase liquid chromatography to fractionate TNS-(S)n-STK (the chemical formula 3). It is noted that a simple dimer (TNS-STN) with n=0 is also generated at this stage, and a mixture of compounds wherein n is an integer including 0 is obtained. The fractionated mixture was further developed by reverse phase liquid chromatography to obtain TNS-S-STN (the chemical formula 4).

[Formula 4]

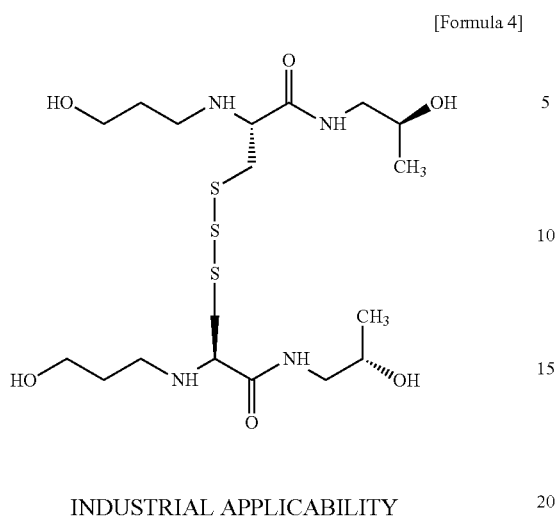

[Formula 1]

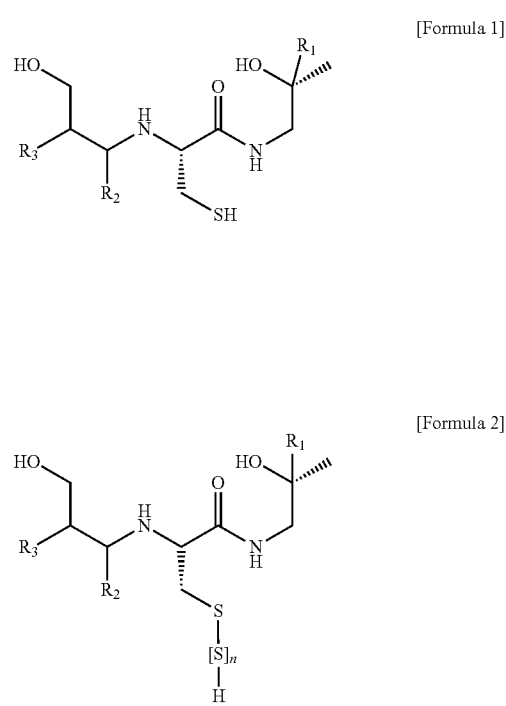

[Formula 2]

[Formula 3]

-continued

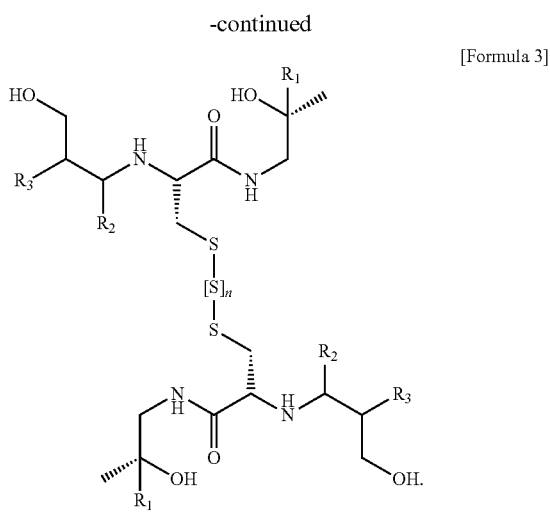

INDUSTRIAL APPLICABILITY

The compound according to the present invention can be used as a therapeutic or preventive agent for cerebral amyloidosis associated with amyloid aggregation such as Alzheimer's disease and cerebral neurodegenerative diseases associated with cerebral ischemia.

The invention claimed is:

1. A compound represented by any of the chemical formula 1 wherein $R_1$, $R_2$, and $R_3$ are each independently a hydrogen atom, a halogen atom, or an aliphatic hydrocarbon group having a carbon number of from 1 to 10, the chemical formula 2 wherein $R_1$, $R_2$, and $R_3$ are each independently a hydrogen atom, a halogen atom, or an aliphatic hydrocarbon group having a carbon number of from 1 to 10, and n is an integer of 1 or more, or the chemical formula 3 wherein $R_1$, $R_2$, and $R_3$ are each independently a hydrogen atom, a halogen atom, or an aliphatic hydrocarbon group having a carbon number of from 1 to 10, and n is an integer of 1 or more, and a pharmaceutically acceptable salt thereof 2. A GAPDH aggregation inhibitor including as an active ingredient one or more compounds selected from the group consisting of a compound represented by any of the chemical formula 1 wherein $R_1$, $R_2$, and $R_3$ are each independently a hydrogen atom, a halogen atom, an aliphatic hydrocarbon group having a carbon number of from 1 to 10, the chemical formula 2 wherein $R_1$, $R_2$, and $R_3$ are each independently a hydrogen atom, a halogen atom, or an aliphatic hydrocarbon group having a carbon number of from 1 to 10, and n is an integer of 1 or more, or the chemical formula 3 wherein $R_1$, $R_2$, and $R_3$ are each independently a hydrogen atom, a halogen atom, or an aliphatic hydrocarbon group having a carbon number of from 1 to 10, and n is an integer of 1 or more, and a pharmaceutically acceptable salt thereof

[Formula 1]

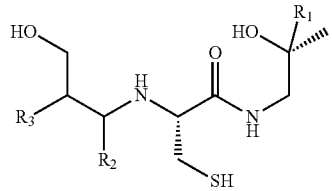

[Formula 2]

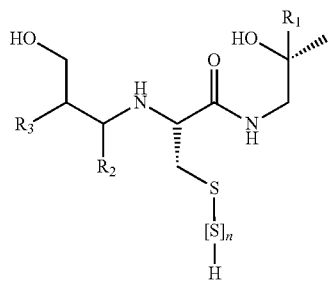

[Formula 3]

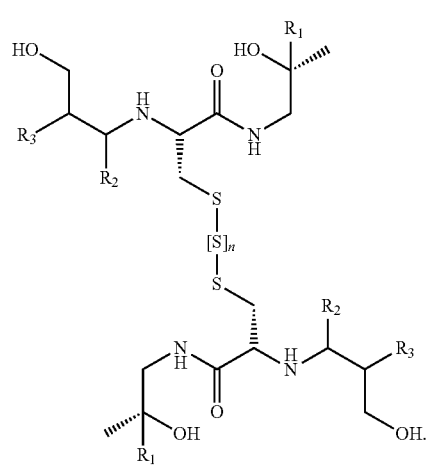

3. A pharmaceutical composition comprising the compound according to claim 1.

* * * * *

```
                         SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: GAPDH Aggregation inhibitor

<400> SEQUENCE: 1

Ser Asn Ala Ser Cys Thr Thr Asn Ala Leu
1               5                   10
```